(12) United States Patent
Regnier

(10) Patent No.: US 11,181,296 B2
(45) Date of Patent: Nov. 23, 2021

(54) SYSTEM AND METHOD FOR IMPROVING AIR-QUALITY OF A SPACE SERVICED BY AN EXIT REGISTER

(71) Applicant: Jon O. Regnier, Santa Ana, CA (US)

(72) Inventor: Jon O. Regnier, Santa Ana, CA (US)

( * ) Notice: Subject to any disclaimer, the term of this patent is extended or adjusted under 35 U.S.C. 154(b) by 189 days.

(21) Appl. No.: 16/389,881

(22) Filed: Apr. 19, 2019

(65) Prior Publication Data

US 2019/0323725 A1  Oct. 24, 2019

Related U.S. Application Data

(60) Provisional application No. 62/762,062, filed on Apr. 19, 2018.

(51) Int. Cl.
*F24F 13/08* (2006.01)
*B01D 46/00* (2006.01)
*B01D 53/04* (2006.01)
*A61L 9/014* (2006.01)

(52) U.S. Cl.
CPC ............ *F24F 13/084* (2013.01); *A61L 9/014* (2013.01); *B01D 46/0005* (2013.01);
(Continued)

(58) Field of Classification Search
CPC ....... F24F 13/084; F24F 13/085; A61L 9/014; A61L 2209/14; A61L 2209/15; A61L 2209/16; A61L 2209/22; B01D 46/0005; B01D 46/0028; B01D 46/0036; B01D 46/0038; B01D 53/04; B01D 2253/102; B01D 2259/4508; B01D 2265/02; B01D 2279/50
(Continued)

(56) References Cited

U.S. PATENT DOCUMENTS 2,575,499 A * 11/1951 Manow ................. B01D 46/10
                                                                    55/422
2,825,500 A *  3/1958 McLean ............ H05K 7/20181
                                                                    55/470
(Continued)

OTHER PUBLICATIONS

"K Push Magnetic Catches" by Richelieu Hardware—HQ (Published Oct. 17, 2016) Accessible at: https://www.youtube.com/watch?v=fLuZfAPfh8c (Year: 2016).*

*Primary Examiner* — Justin M Jonaitis
(74) *Attorney, Agent, or Firm* — Jacob M. Ward; Ward Law Office LLC

(57) ABSTRACT

A system for improving an air-quality of a given space serviced by an exit register of an AC system including a base frame device that is configured to engage the exit register, a metal base frame section for engaging the base frame device with a perimeter of the exit register. A register cover device that is configured to magnetically engage the base frame device. The register cover device having a plurality of alternating open space portions, a plurality of air diverting fin segments, and a magnet holder implement. The magnet holder implement includes at least four magnet holders that are disposed on each end corner portion of the register cover device. At least four height adjustable magnets are disposed on each of the magnet holders, wherein each of the height adjustable magnets is configured to magnetically engage the register cover device with the base frame device.

20 Claims, 5 Drawing Sheets

(52) U.S. Cl.
CPC ..... *B01D 46/0028* (2013.01); *B01D 46/0036* (2013.01); *B01D 46/0038* (2013.01); *B01D 53/04* (2013.01); *F24F 13/085* (2013.01); *A61L 2209/14* (2013.01); *A61L 2209/15* (2013.01); *A61L 2209/16* (2013.01); *A61L 2209/22* (2013.01); *B01D 2253/102* (2013.01); *B01D 2259/4508* (2013.01); *B01D 2265/02* (2013.01); *B01D 2279/50* (2013.01)

(58) Field of Classification Search
USPC .......................................... 454/358; 422/122
See application file for complete search history.

(56) References Cited

U.S. PATENT DOCUMENTS

| | | | | |
|---|---|---|---|---|
| 4,981,501 | A * | 1/1991 | Von Blucher | B01D 39/00 55/477 |
| 5,525,145 | A * | 6/1996 | Hodge | B01D 46/001 96/17 |
| 5,720,660 | A * | 2/1998 | Benedetto | F24F 13/08 454/284 |
| 8,460,419 | B1 * | 6/2013 | Hobbs | B01D 46/10 55/385.2 |
| 9,726,395 | B2 * | 8/2017 | Hammer | F24F 13/082 |
| 10,543,445 | B2 * | 1/2020 | Branzelle | B01D 46/2411 |
| 2005/0161387 | A1 * | 7/2005 | Van de Graaf | B01D 46/0091 210/321.6 |
| 2014/0373493 | A1 * | 12/2014 | Cannon | B01D 46/0005 55/490.1 |

* cited by examiner

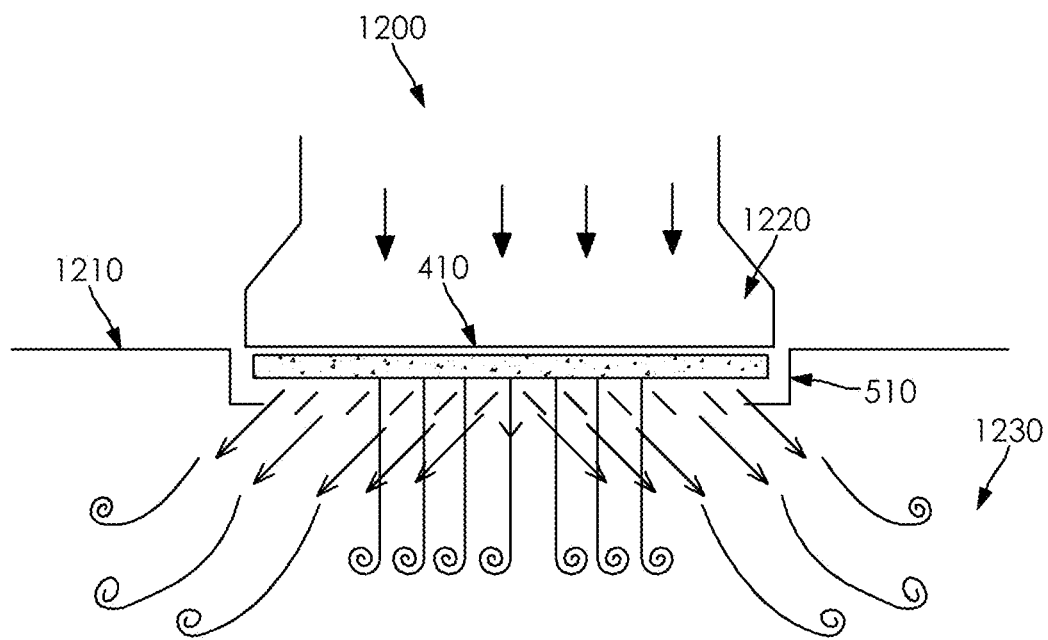
FIG. 12
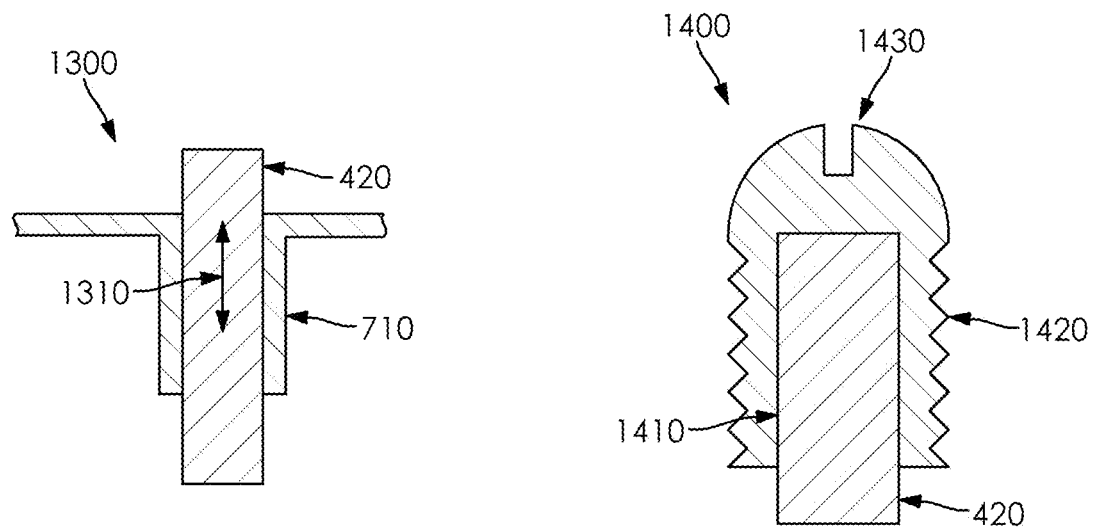
FIG. 13  FIG. 14

SYSTEM AND METHOD FOR IMPROVING AIR-QUALITY OF A SPACE SERVICED BY AN EXIT REGISTER

CROSS-REFERENCE TO RELATED APPLICATIONS

The present Utility patent application claims priority benefit of the U.S. provisional application for patent Ser. No. 62/762,062 entitled "Retrofit register vent air filter cover, design and utility innovation", filed on Apr. 19, 2018 under 35 U.S.C. 119(e). The contents of this related provisional application are incorporated herein by reference for all purposes to the extent that such subject matter is not inconsistent herewith or limiting hereof.

RELATED CO-PENDING U.S. PATENT APPLICATIONS

Not applicable.

INCORPORATION BY REFERENCE OF SEQUENCE LISTING PROVIDED AS A TEXT FILE

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to air venting systems. More particularly, certain embodiments of the invention relate to air vent system cover.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that cooled or heated air forced through heating, ventilation and air-conditioning (HVAC) systems is generally ducted to one or more registers, vents or diffusers, which are located in predetermined locations throughout a residential building such as a house or apartment, or a commercial building such as stores, offices, etc. HVAC systems generally have a series of air passageways or ducts contained within the building's walls, floors, ceilings and attic crawl spaces. The ducts carry the heated or cooled air to registers located various rooms of the building such as living and/or work areas. The ducts may engage registers attached to the back side of an interior surface such as, sheetrock, ceiling, wallboard, a finished or un-finished surface, etc. at openings designed for the register. The register may attach to a wallboard by screws, nails, anchors, etc.

Typical centralized air heating and cooling systems use ducting to transport air to various rooms from a centrally located heating and cooling system. The heated or cooled air exits the ducts into various rooms in residential or commercial buildings through air vents. Air vents perform two main functions including directing air into the various rooms and the other is to open and limit the airflow to a room. Central air heating and cooling systems are equipped with filters located at the main heating and cooling system. These filters may remove most of the particles in the air. Some particles can still be present in the air and will exit into the room through the air vents. Typically air that circulates through the HVAC ducting and blower systems may be filtered through the return air filter provision. The air filter provisions effectiveness, is determined by the type and quality of the filter used and the overall condition of the HVAC system and the associated ducting through which the air flows, along with the condition of the exit registers. And the condition of the overall environment the system is servicing whether it be a clean environment or perhaps a very dirty dusty environment. As a result of these many and varied conditions, the exit airflow from the exit vent registers is likely to be substantially contaminated or causing airborne particulate contamination, even if the return air filters are in place and are regularly maintained according to industry standards. Typical exit register covers with air filters to improve the air-quality of any given space serviced by the exit register have utility limitations or omissions that may hinder full and convenient optimization and functionality of the exit register cover.

Furthermore, typical HVAC air filters may be installed at return air grills or directly adjacent to the HVAC blower unit. The air is pulled into the HVAC system and then delivered through a series of air ducts to service each room in a house or apartment or building as designed. The initial intake air typically employs a filter. This air system circulates and conditions the air while the system is running. Within this HVAC blower ducting system, typically there exist between 10 feet and 100 feet or more of air ducting that delivers the air to any given room or space. These ducting systems are usually concealed in attic spaces or wall and ceiling void spaces before exiting into the given spaces the ducting provides air flow too. Unfortunately these concealed ducting air passages overtime can get very dirty and contaminated with every kind of dust particles, living or dead biological material, mold etc. one can imagine. It may be very common for these ducting blower systems to become compromised. For example, the intake air filter may not be installed properly. Or the intake air filter may not be replaced or cleaned as needed, and thus clog or contaminate the air conditioning. Or there may be unseen gaps in the ducting system that can significantly cause the air in the ducting system to become contaminated in route to the room exit points. All of these factors come into play to adversely affect the overall quality of indoor air that is being conditioned through the HVAC. It is well known that poor indoor air quality is a massive health problem that continues to worsen.

Typical exit registers tend to blow the air in one general direction even though most registers have adjustment louvers. So that once the louvre position has been set, the exit air may take on a particular persistent pattern of airflow into any given space. This particular persistent pattern may kick up or stir up existing room dust from the floor and other and all surfaces, and thereafter may create a circular pattern that continuously circulates existing room airborne particulate contamination and particulate/biologic contamination emanating from the ducting system itself. And if the spaces are not near the return air filter provision, these circular air patterns created by the HVAC exit air, may not receive any filtration. As a result, the circular pattern of air containing the particulate contamination may pose significant health risks for individuals who may be occupying or sleeping in those spaces. Children and the elderly in particular are at high risk. Also, persistent direct airflow, which is generally typical with conventional exit registers, even if the airflow is relatively dust free, this persistent direct airflow can be harmful to humans, especially young children or elderly in sleeping spaces exposed to prolonged exposure. For example, personal experiences with these air flow/dust circulation patterns from HVAC systems, resulted in the development of asthma in children since they were born.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIG. 12 is an illustration of an exemplary air flow through the venting system, in accordance with an embodiment of the present invention;

FIG. 13 is an illustration 1300 of an exemplary precision fitting magnet holder, in accordance with an embodiment of the present invention; and FIG. 14 is an illustration 1400 of an exemplary magnet holder with screw cap, in accordance with an embodiment of the present invention.

Figure 1:
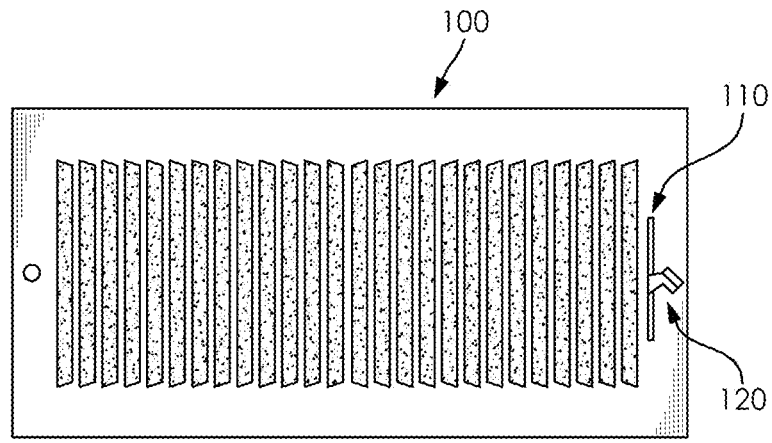
FIG. 1 is an illustration of a typical metal register vent cover.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settled law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of Claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub-combination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" include the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, are generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of. or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising" And "contain" and variations of them—Such terms are open-ended and mean "including but not limited to". When employed in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. sctn. 112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

All terms of exemplary language (e.g., including, without limitation, "such as", "like", "for example", "for instance", "similar to", etc.) are not exclusive of any other, potentially, unrelated, types of examples; thus, implicitly mean "by way of example, and not limitation . . . ", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Moreover, any claim limitation phrased in functional limitation terms covered by 35 USC § 112(6) (post AIA 112(f)) which has a preamble invoking the closed terms "consisting of," or "consisting essentially of," should be understood to mean that the corresponding structure(s) disclosed herein define the exact metes and bounds of what the so claimed invention embodiment(s) consists of, or consisting essentially of, to the exclusion of any other elements which do not materially affect the intended purpose of the so claimed embodiment(s).

Devices or system modules that are in at least general communication with each other need not be in continuous communication with each other, unless expressly specified otherwise. In addition, devices or system modules that are in at least general communication with each other may communicate directly or indirectly through one or more intermediaries. Moreover, it is understood that any system components described or named in any embodiment or claimed herein may be grouped or sub-grouped (and accordingly implicitly renamed) in any combination or sub-combination as those skilled in the art can imagine as suitable for the particular application, and still be within the scope and spirit of the claimed embodiments of the present invention. For an example of what this means, if the invention was a controller of a motor and a valve and the embodiments and claims articulated those components as being separately grouped and connected, applying the foregoing would mean that such an invention and claims would also implicitly cover the valve being grouped inside the motor and the controller being a remote controller with no direct physical connection to the motor or internalized valve, as such the claimed invention is contemplated to cover all ways of grouping and/or adding of intermediate components or systems that still substantially achieve the intended result of the invention.

A description of an embodiment with several components in communication with each other does not imply that all such components are required. On the contrary a variety of optional components is described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Some embodiments of the present invention and variations thereof, relate to air venting systems. In one embodiment of the present invention, the system may comprise a register, grille, or vent cover device and a secondary air filtration implement. The system may be installed as retrofit over existing registers or to install as a replacement or new construction at a ducting air exit point. In some embodiments, the system may further comprise a blank open metal frame, which may be fastened with approximately two screws. The blank open metal frame may include, but not limited to, a rectangle or square metal frame, with approximately ⅛" turned over sides, inside and out, and securely fastened with two screws to a wall or floor surface over an exit ducting plenum. Once the frame is installed it becomes the new open metal base by which a new magnetic register/grille cover and/or secondary air filtration may be installed by magnetic force on top of the new metal frame.

In other embodiments, the system may be installed as retrofit. However, the device is recommended to be installed as a replacement or new construction for the following reasons: Existing covers of ducting systems such as air vents, grilles, and air registers themselves get dirty and may necessitate cleaning regularly to the extent possible. In order to clean the ducting systems, an existing air register/grille/vent cover may have to be taken out to access the plenum/ducting behind the existing air register/grille/vent cover. This entails the air register/grille/vent cover to be removed, typically by removing the two register fastening screws. However easy this may sound, it may be difficult and problematic, as these existing air register/grille/vent covers may be in difficult to reach areas or there may be many layers of paint over these existing registers and essentially glued to the surface, making it very difficult for a homeowner or even a service provider to remove the register. As a result of these potential difficulties and other mitigating circumstances, most people never remove the registers in order to clean, maintain, and/or inspect the ducting system or the register/grille covers. As a result, there may exist high levels of dust accumulation and other contamination over the course of many years. Installing the metal open frame in place of the existing registers/grilles, provides for easy, almost instant access to the interior ducting system for cleaning, maintenance, and/or inspection as recommended. This may be accomplished by simply lifting off magnetically attached register/grille cover and/or filter appliance without having to unscrew any securing means. By removing the existing register and replacing it with the new register/grille cover and/or filter appliance as replacement or new construction, the system may provide for ease of maintenance, better overall performance and longevity of the HVAC system. Also, by removing old existing register cover and installing new appliance consisting of open frame, filter medium and magnetically attached cover, one register is eliminated, resulting in less back pressure to the HVAC system and thus greater airflow through the new appliance and filter medium.

Having installed the metal frame base, installing the new register/grille/vent cover and/or filter appliance may be accomplished as follows: The new register/grille/vent cover with filter appliance may comprise of, but not limited to a plastic or metal register/grille/vent cover having grills arranged with a series of fins that are but not limited to approximately half inch (½") wide, between half inch (½") open areas. The fins may be roughly equally separated from a proximate middle open area and are generally angled away from each other at a more or less thirty degrees (30°) plane. The register/grille/vent cover with the fins may provide maximum airflow while supporting and containing the filter appliance. The register/grille/vent cover may further include adjustable magnets at a proximate, but not limited to roughly four (4) corners of the register cover at more or less three fourth inch (¾") from an end portion of each corner. The adjustable magnets may comprise of one or more magnets disposed at the end portion of each corner. The register/grille/vent cover may stand more or less three fourth (¾) of an inch high. The length and width of the register cover may vary according to the length and width of the exit plenums they will be attached to, as the industry standard has many size openings. On the backside of the register cover, the filter appliance including but not limited to a particulate filter may be installed just about inside from wall to wall. The particulate filter may be more or less three eighth inch (⅜") high and may have pre-existing cut out holes of roughly half inch (½") in diameter to be placed over the one or more magnet holders. More or less four (4) corner magnet/stud areas. For example, if there are four (4) adjustable magnet holders on each corner of the register/grille/vent cover, the filter appliance may comprise of four (4) pre-cut holes corresponding to the placement of the adjustable magnet. If there are six (6) adjustable magnet holders on each corner and a proximate middle portion of the register cover, the filter appliance may comprise of six (6) pre-cut holes corresponding to the placement of the adjustable magnet, and so on.

In additional embodiments, the new metal base frame may be used over existing aluminum registers to become the base for the retrofit new register cover and/or filter appliance. For example, aluminum registers are used at times in areas subject to moisture.

In further embodiments, the adjustable magnets have height adjustment capabilities. The magnets are installed into precision plastic stud holes that generally allow the magnets to move up and down inside the plastic stud holes, but at the same time have enough friction. The height adjustable magnet implement may comprise of, but not limited to, a proximate cylindrical or round shaped magnet, a roughly square or rectangular shaped magnet, etc. Once the register/grille/vent cover and filter appliance has been installed and positioned, the register/grille/vent cover will meet flush against the adjoining wall or floor, and to either the existing register or new metal frame base. The magnets may thereafter stay in place tight, as a custom fit appliance. The height adjustable magnets may be necessary because the retrofit over existing registers may entail height adjustment as not all existing vent registers are of the same height. Some existing register/grille/vent covers are as thin as about 1/16" or as thick as about 1/4". Thus in order for the register/grille/vent cover and filter appliance to completely encompass the old register or the new open metal frame, the magnets may be able to substantially adjust to those variations in height to achieve as close to air tight as possible, and for direct magnet to metal contact attachment. The result is, when the system is installed properly, the system may provide for the ability to filter, soften and disperse the air coming out of any exit register where the new register cover and filter appliance is installed. Provide for easy replacement and/or cleaning of the filter appliance and/or register cover. And, to provide easy access to the plenum ducting system for cleaning and inspection.

In some embodiments, in order to use the new register/grille/vent cover with filter appliance over existing registers, the new register/grille/vent cover with filter appliance may be designed to accommodate typical louver adjustment arm. The louver adjustment arms may typically extend out from the plane of the existing register by as much as more or less one and a half inch (1½"), and the louver adjustment arms may be found at varying areas depending on the type and age of the existing register. As part of the overall design of the new register cover with filter appliance, the register cover has more or less half inch (½") open areas between the more or less half inch (½") air diverting fins. The roughly half inch (½") open areas are large enough and spaced enough to accommodate any louver adjustment arms that may be purchased new or appear on older register appliances. These open area access points are vital for the retrofit cover so that the existing register can still be adjusted via the louver handle. For example, the filter appliance will have to be cut at the location of the louver arm to pass though or have factory precuts.

In other embodiments, to reduce circular air patterns and limit existing room dust from becoming airborne, air exiting from the register will first be filtered through the filter media. This first step will soften and balance out the register exit air. The air will then pass through the register cover/grill. As has been previously explained, the grill has more or less half inch (½") open spaces and more or less half inch (½") and roughly thirty degrees (30°) disbursal fins that alternate between the open spaces. The dispersal fins may be separated in the middle of the register cover, where half may divert air to the right and half may divert air to the left. Combining these design elements into the new register cover and filter appliance significantly improves, softens, and disburses the air entering any room where the new system is installed. And, thus may reduce the potential for associated persistent air pattern circulation problems. Further, the left and right side of the new register cover comprises one or more indentations. The one or more indented areas are configured as filter holding areas which may make installing or removing the filter appliance much easier.

In some embodiments, the register cover or filter frame may further comprise a removable scented pad which may impart an aroma or therapeutic fragrance to the air blowing through the register. Additionally, the filter appliance may incorporate, but not limited to, an antibacterial filter media, allergy-free filter media, and/or odor reduction filter media.

In one embodiment, the register/grille/vent cover and filter appliance engages in seconds to the existing register through the use of the adjustable magnets. The register/grille/vent cover may be made from a metal material. Alternatively, the register/grille/vent cover may be made from a plastic material, which may be molded from a plastic composite material, such as, but not limited to, PVC, ABS, etc. The register/grille/vent cover may take the form of, but not limited to, a square, rectangular, spherical and/or quadrilateral shape that has a top, a bottom and more or less four (4) sidewalls that when put in place, may cover an entire register. Alternatively, the register/grille/vent cover may take any desired shape and size to accommodate varying shapes and sizes of existing register/grille/vent covers. When placed over a register, the bottom end portion of the sides of the register cover come in contact with the surface of a floor, a wallboard, a ceiling, or other finished or un-finished surface, that surrounds the register. The register cover may form a tight and flush seal over the register, which may eliminate the transfer of air from leaving and/or entering the register. The register cover is attached to the register through the one or more securing magnetic element that may form a magnetic attraction between the register cover and the register.

In an alternative embodiment, dampers may be provided in the register cover to control the flow of air through the register. The register cover may be provided with a plurality of closely spaced louvers that are controlled by an external lever to adjust the louvers in an open position, a closed position or a position that is set by a user. The closed position of this type of damper may have the louvers closely overlap each other to impede the flow of air through the air register. In the closed position, heated or cooled air circulated by the HVAC system may be re-directed to another portion of a residential or commercial building.

The present invention will now be described in detail with reference to embodiments thereof as illustrated in the accompanying drawings. The device may include register vent cover and a secondary air filter implement.

FIG. 1 is an illustration of a typical metal register vent cover 100. A typical metal register vent cover may include a louver arm 120 and a louver arm slot 110.

Figure 2:
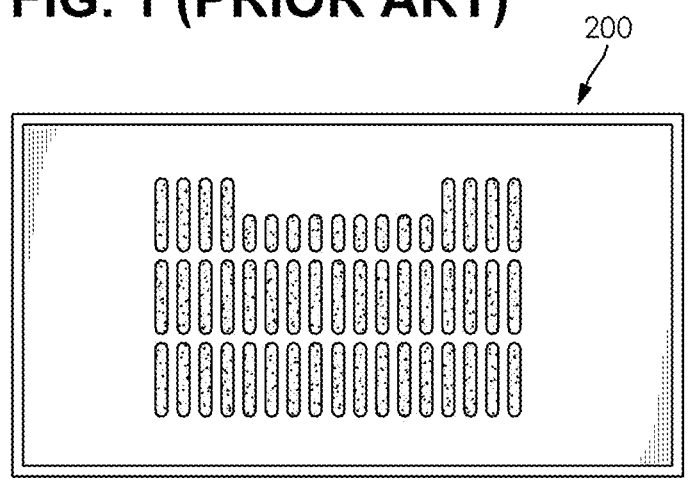
FIG. 2 is a front view of a typical vent cover.

FIG. 2 is a front view of another typical vent cover 200.

Figure 3:
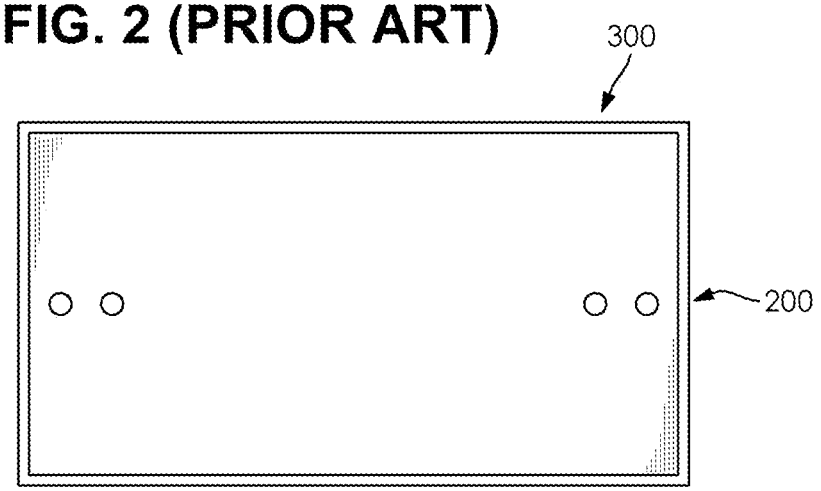
FIG. 3 is a back side view of the typical vent cover shown in FIG. 2.

FIG. 3 is a back side view 300 of the typical vent cover shown in FIG. 2.

Figure 4:
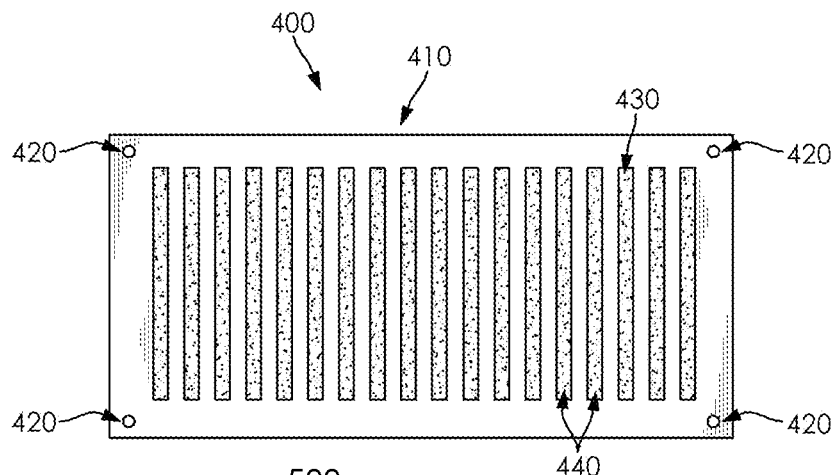
FIG. 4 is an illustration of an exemplary venting system with a register/grille/vent cover device, in accordance with an embodiment of the present invention.

FIG. 4 is an illustration of an exemplary venting system 400 with a register/grille/vent cover device 410, in accordance with an embodiment of the present invention. In the present embodiment, the register/grille/vent cover device 410 may comprise a plurality of height adjustable magnet implement 420, a plurality of alternating open spaces with air diverting fins 440, and a plurality of open spaces 430 configured to accommodate existing louver handles. The height adjustable magnet implement 420 may comprise at least one of, a proximate cylindrical or round shaped magnet and a roughly square or rectangular shaped magnet. The height adjustable magnet implement 420 may further comprise of at least four (4) height adjustable magnets as shown, each height adjustable magnet being disposed on an end portion of a corner of the register cover device. The magnets 420 may be installed into, but not limited to, precision plastic stud holes that generally allow the magnets 420 to move up and down inside the plastic stud holes, but at the same time have enough friction. The height adjustable magnets may be necessary because the retrofit over existing registers may entail height adjustment, as not all existing vent registers are of the same height. Some existing register/grille/vent covers are as thin as about 1/16" or as thick as about 1/4". Thus in order for the register/grille/vent cover and filter appliance to generally adapt to old registers or the new open metal frame, the magnets may be configured to substantially adjust to those height variations to achieve as close to air tight as possible, and for direct magnet to metal contact/coupling attachment/engagement. The result is, when the system is installed properly, the system may provide for the ability to filter, soften and disperse the air coming out of any exit register where the new register cover and filter appliance is installed. Provide for easy replacement and/or cleaning of the filter appliance and/or register cover. Further, to provide easy access to the plenum ducting system for cleaning and inspection. Once the register cover device 410 has been installed and positioned, the register cover device 410 will meet flush against the adjoining wall or floor, and to either the existing register or new metal frame base. The magnets 420 may thereafter stay in place tight, as a custom fit appliance. The alternating open spaces with air diverting fins 440 may comprise of more or less half inch (½") open spaces. The air diverting fins 440 may comprise of roughly half inch (½") width and about thirty (30) degrees incline air diverting fins.

In some embodiments, the register/grille/vent cover may be made from a plastic material, which may be molded from a composite material, such as, but not limited to, PVC, ABS, urethane resin, etc. Alternatively, the register cover device 410 may be made from a metal material including but not limited to, aluminum, steel, etc. Further, the length and width of the register cover device 410 may vary to match existing duct opening.

Figure 5:
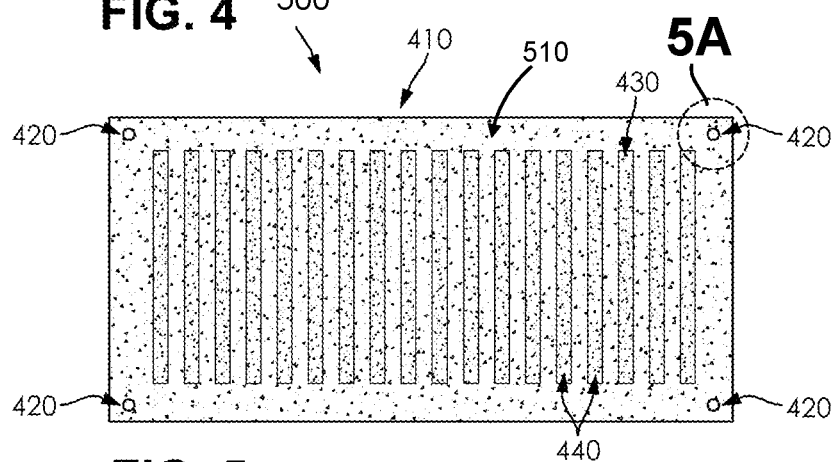
FIG. 5 is a back view illustration of the exemplary register/grille/vent cover device, in accordance with an embodiment of the present invention.
Figure 5A:
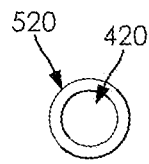

FIG. 5 is a back view illustration 500 of the exemplary register/grille/vent cover device 410, in accordance with an embodiment of the present invention. In the present embodiment shown, the back portion of the register/grille/vent cover device 410 comprises at least one or more indentations 530. The one or more indented areas are configured as filter appliance 510 holding areas which may make installing or removing the filter appliance 510 much easier. The filter appliance 510 mostly covers a wall to wall back side portion of the register cover device 410. The filter appliance 510 may comprise a plurality of pre-cut holes 520 corresponding to the placement of the adjustable magnet 420 on the register cover 410. For example, if there are about four (4) adjustable magnet holders on each corner of the register cover, the filter appliance 510 may comprise of roughly four (4) pre-cut holes corresponding to the placement of the adjustable magnet. If there are about six (6) adjustable magnet holders on each corner and a proximate middle portion of the register cover, the filter appliance 510 may comprise of roughly six (6) pre-cut holes corresponding to the placement of the adjustable magnet, and so on. FIG. 5*a* shows an exploded top view of a pre-cut hole 520 corresponding to an adjustable magnet 420.

In additional embodiments, the filter appliance 510 may comprise a removable filter frame. The filter frame housing a filter medium is receivable in one or more indentations or filter holding areas of the register cover. The filter holding areas may comprise of securing elements such as, but not limited to Velcro®, snaps, buttons, adhesive, etc. to secure the filter frame. The filter frame may comprise of a plurality of pre-cut holes 520 corresponding to the number of adjustable magnet 420 holders on the register cover 410. The filter frame may further comprise of one or more filter frames corresponding to the number of indentations or filter holding areas. The filter frame may include multiple entry and exit openings for filtered air to pass though. The filter holding areas may comprise of a channel opening formed within the sidewalls of the register cover wherein the filter frame is receivable and removable through the channel. The filter holding areas may further comprise of securing elements such as, but not limited to Velcro®, snaps, buttons, adhesive, etc. to secure the filter frame.

In some embodiments, the register cover or filter frame may further comprise a removable scented pad which may impart an aroma or therapeutic fragrance to the air blowing through the register. Additionally, the filter appliance 510 may incorporate, but not limited to, activated carbon filters configured to chemically absorb contaminants, impurities and light odors from the air. An antibacterial filter media that are configured to generally inhibit the growth of microorganisms while substantially ridding the air of others such as, but not limited to, mold and mildew. An allergy-free filter media that are configured to capture dust, lint, smoke, mold, mildew and pollen, and/or odor reduction filter media.

Figure 6:
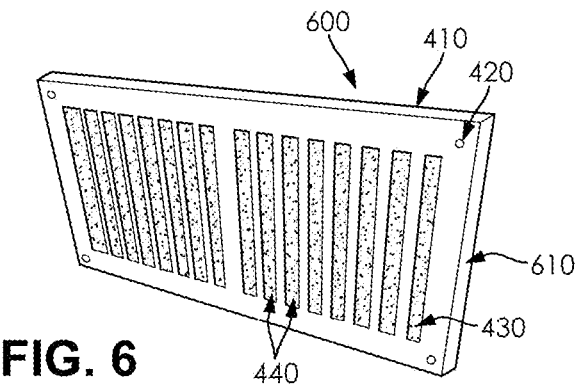
FIG. 6 is a 3-dimensional (3D) view illustration of the exemplary register/grille/vent cover device, in accordance with an embodiment of the present invention.

FIG. 6 is a 3-dimensional (3D) view illustration 600 of an exemplary register/grille/vent cover device 410, in accordance with an embodiment of the present invention. In the present embodiment shown, the register/grille cover device 410 may comprise a height adjustable magnet implement 420, a plurality of alternating open spaces with air diverting fins 430, an open space 440 to accommodate an existing louver handle, and a device sidewall 610. The device sidewall 610 may comprise a height of more or less three fourth inch (¾"). The height adjustable magnet implement 420 may comprise at least one of, a proximate cylindrical or round shaped magnet and a roughly square or rectangular shaped magnet. The height adjustable magnets may further comprise about one fourth by one half inch (¼"×½") height adjustable magnets. The height adjustable magnet implement 420 may further comprise of at least four (4) height adjustable magnets, each height adjustable magnet being disposed on an end portion of a corner of the register cover device 410. The height adjustable magnets may be disposed three-fourth by three-fourth inch (¾"×¾") from an end portion of the corner of the device. The alternating open space and/or fins may be at roughly thirty (30) degrees incline. In one embodiment, roughly half of the fins may be generally pointed to a proximate left side and roughly half of the fins may be pointed to a proximate right side of the register/grille cover device.

Figure 7A:
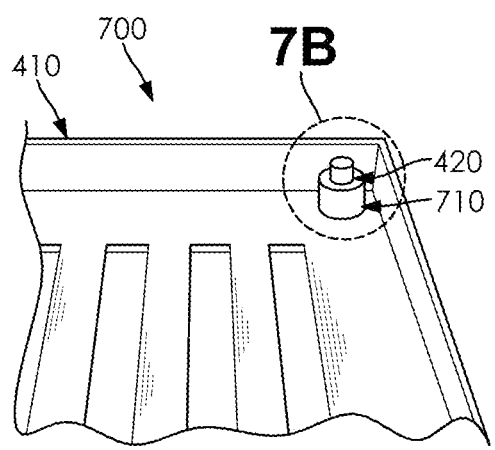
FIG. 7a-7b is a back corner view of the exemplary register/grille/vent cover, in accordance with an embodiment of the present invention.
Figure 7B:
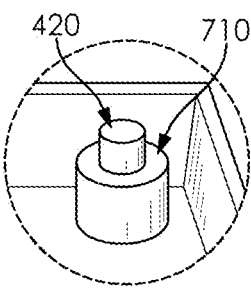

FIG. 7*a* is a back corner view 700 of the exemplary register/grille/vent cover 410, in accordance with an embodiment of the present invention. In the present embodiment shown, the register cover device 410 may comprise a height adjustable magnet implement 420 installed into a magnet holder 710. The height adjustable magnet implement 420 may comprise at least, but not limited to a proximate cylindrical shaped magnet. Alternatively, the height adjustable magnet implement 420 may comprise at least one of, but not limited to, a proximate square or rectangular shaped magnet, a proximate triangular shaped magnet, a magnet with five (5) or more sides and a magnet with wavy sides. The height adjustable magnet implement 420 may be disposed on an end portion of a corner of the register cover device. The height adjustable magnet implement 420 may be installed into a magnet holder 710 that is configured to allow the height adjustable magnet implement 420 to move up and down inside the magnet holder 410, but at the same time have enough friction. For example, magnet holder 710 may be precision fitting over magnet implement 420 to provide for up and down movement to achieve 410 height adjustment while at the same time applying enough friction to hold magnet implement 420 tight, once proper height adjustment is achieved. In additional embodiments, magnet implement 420 height adjustment may be achieved by other mechanical means such as, but not limited, magnet holder with screw head. FIG. 7b shows an exploded top view of a magnet holder 710 with a corresponding height adjustable magnet 420.

Figure 8:
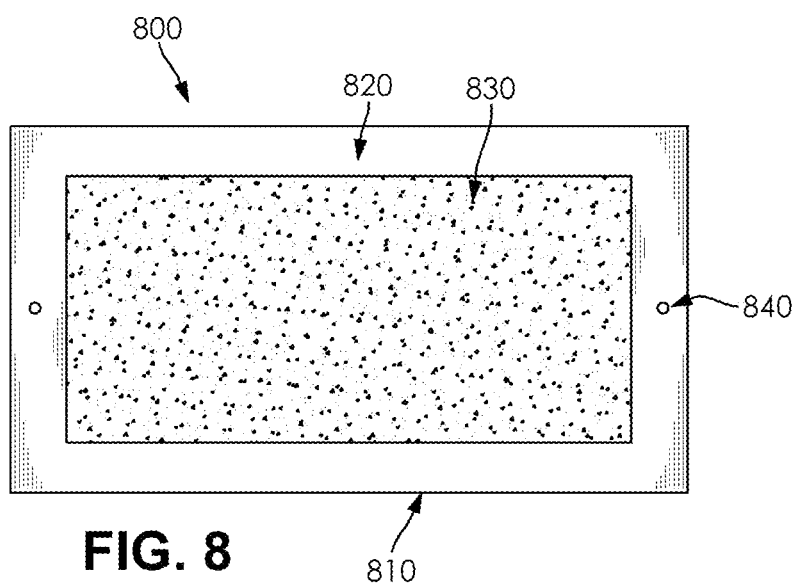
FIG. 8 is an illustration of an exemplary register cover base frame, in accordance with an embodiment of the present invention.

FIG. 8 is an illustration 800 of an exemplary register cover base frame 810, in accordance with an embodiment of the present invention. In the present embodiment shown, the register cover base frame 810 may comprise a metal base 820, a blank or open base frame space 830 to ducting plenum, and a base frame securing holes 840. The register cover base frame 810 dimensions may include 1¼×1¼×⅛. The register cover base frame 810 may replace existing registers as these existing registers may be in difficult to reach areas or there may be many layers of paint over these existing registers and essentially glued to the surface, making it very difficult for a homeowner or even a service provider to remove the registers. As a result of these potential difficulties and other mitigating circumstances, most people never remove the registers in order to clean and maintain/inspect the ducting system or the register covers. As a result, high levels of dust and other contaminants may accumulate over the course of many years. Therefore installing the register cover base frame 810 in place of the existing registers, provides for easy, almost instant access to the interior ducting system for cleaning and inspection as needed and recommended, by simply lifting off the magnetically attached register cover and/or filter appliance. Further, by removing the existing register and using the new register cover and/or filter appliance as replacement or new construction, the system may provide for ease of maintenance, better overall performance and longevity of a corresponding HVAC system.

Figure 9:
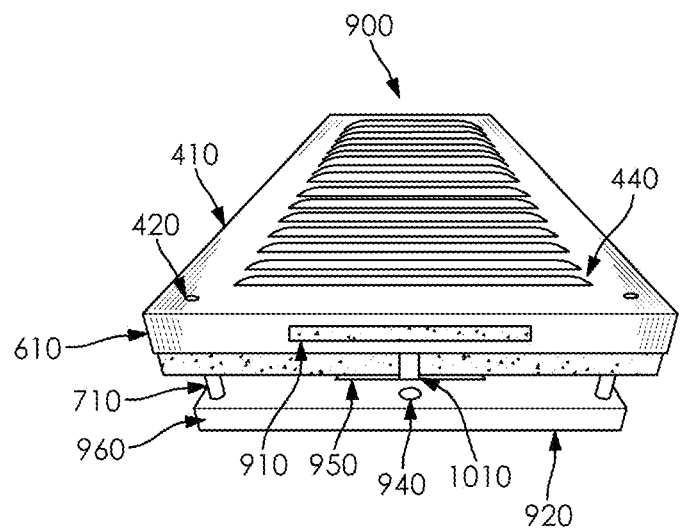
FIG. 9 is an illustration of the exemplary venting system, in accordance with an embodiment of the present invention.

FIG. 9 is an illustration of an exemplary venting system 900, in accordance with an embodiment of the present invention. In the present embodiment shown, the venting system 900 may comprise a register/grille/vent cover device 410 installed over an existing/retrofit register 920. The register/grille/vent cover device 410 shown may comprise a height adjustable magnet implement 420 disposed on an end portion of a corner of the register cover device, a sidewall 610 surrounding the device, an upper louver arm slot open space 440 to accommodate existing louver handles, and an indented handle 910 for generally handling the device. The indented handle 910 may include a rubberized grip. The register/grille/vent cover device 410 magnetically attaches to the existing register 920 via the height adjustable magnet implement 420 housed in a magnet holder 710. The existing register 920 having a thickness 960 may be installed on a surface with screws through securing holes 940. The upper louver arm slot device open space 440 is configured to accommodate the upper portion of louver arm 930 of the existing register 920 and allow the lower portion of louver arm 930 to travel through lower louver arm slot 950.

Figure 10:
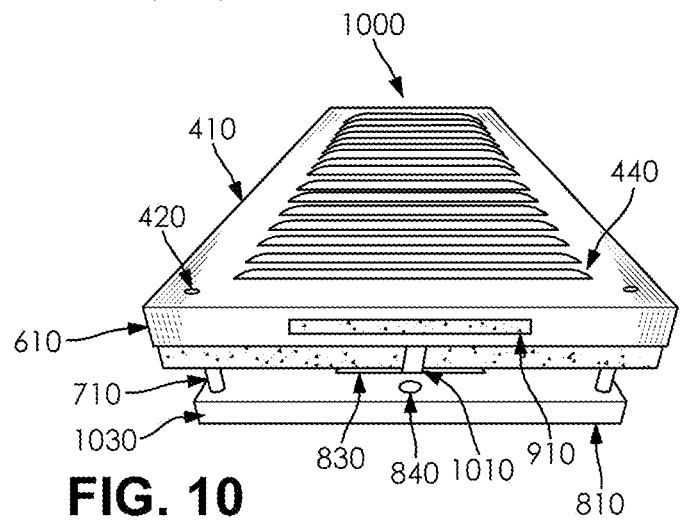
FIG. 10 is an illustration of the exemplary venting system, in accordance with an embodiment of the present invention.

FIG. 10 is an illustration of an exemplary venting system 1000, in accordance with an embodiment of the present invention. In the present embodiment shown, the venting system 1000 may comprise a register/grille/vent cover device 410 installed over a newly installed metal frame base 810. The register/grille/vent cover device 410 shown may comprise a height adjustable magnet implement 420 disposed on an end portion of a corner of the register cover device, a sidewall 610 surrounding the device, and an indented handle 910 for generally handling the device. The indented handle 910 may include a rubberized grip. The register/grille/vent cover device 410 magnetically attaches to the metal frame base 810 via the height adjustable magnet implement 420 housed in a magnet holder 710. The metal frame base 810 having a thickness 1030 may be installed on a surface with screws through securing holes 840. The metal frame base 810 may allow a louver arm 1010 through a base frame open space 830. The device open space 440 is configured to accommodate the louver arm 1010 and allow the louver arm 1010 to travel the base frame open space 830.

Figure 11:
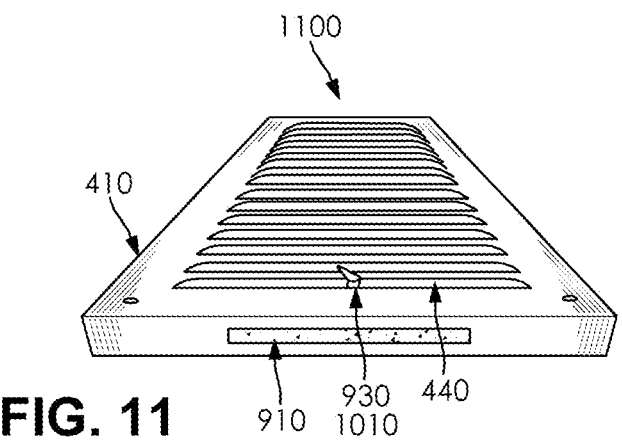
FIG. 11 is a 3D view illustration of the exemplary register/grille/vent cover device installed over an existing register or register cover base frame, in accordance with an embodiment of the present invention.

FIG. 11 is a 3D view 1100 of an installed exemplary register/grille/vent cover device installed over an existing register, in accordance with an embodiment of the present invention. In the present embodiment shown, the register/grille/vent cover device 410 having an indented handle 910 may be installed over an existing register 920 or over a metal frame base 810. The louver arm 930 1010 may be accommodated through the open space/slot 440.

FIG. 12 is an illustration 1200 of an exemplary filtered air through the venting system, in accordance with an embodiment of the present invention. In the present embodiment shown, an air flow 1220 from a ducting system passes through the register/grille/vent cover device 410 and filtered with the filter appliance 510. The result is, when the system is installed properly, the system may provide for the ability to filter, soften and disperse the filtered air 1230 coming out of any exit register where the new register/grille/vent cover device 410 and filter appliance 510 is installed such as a surface 1210. The filtered air 1230 may be dispersed downward and sideways in a safer and more efficient manner than standard industry registers.

FIG. 13 is a close-up illustration of an exemplary precision fitting magnet holder 1300, in accordance with an embodiment of the present invention. In the present embodiment shown, magnet holder 710 may include an inner portion with an inner surface and an outer portion with an outer surface that is precision fitted over magnet implement 420 to provide for up and down movement to achieve cover 410 height adjustment 1310 while at the same time applying enough friction to hold magnet implement 420 tight, once proper height adjustment 1310 is achieved. In another embodiment, the magnet holder may be made of plastic or other material with a precise round or square hole in which a round or square magnet may be inserted with the ability to move the magnet up or down in the hole while having enough hole precision or friction to sufficiently hold the magnet into a fixed position once precision height adjustment has be achieved. Magnet height adjustment will require some force initially to fine tune height adjustment. But once proper height is achieved regular on/off action of filter cover for filter changing, clean or maintenance will not change magnet height thereafter unless additional force is exerting.

FIG. 14 is an illustration of an exemplary alternative magnet holder 1400 with screw cap/head, in accordance with an embodiment of the present invention. In the present embodiment shown, magnet implement 420 height adjustment may be achieved by screw magnet holder 1400 with a screw body 1420, a screw cap/head 1430 and a hollow body 1410. Hollow body 1410 may comprise an outer portion with an outer surface and an inner portion with an inner surface. The shape of the inner portion may include, but not limited to, round, square, rectangular, triangular, or having five (5) or more sides that conform to the type of magnet implement used. The inner surface may be rough, wavy, or smooth configured to be operable for gripping the magnet implement at the same time allow the magnet implement to be height adjusted. The outer portion may include rough outer surface shaped like screw that may be screwed on pre-cut holes 520 of cover 410. Alternatively, the outer portion may comprise a smooth outer surface that may slide through pre-cut holes 520 of cover 410. The screw head cap housing the magnet may adjust the height of the magnet by screwing the cap up and down, thus effectively adjusting the magnet height.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Thus, the present invention is not limited to any particular tangible means of implementation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" or "steps for" claim limitation implies that the broadest initial search on 35 USC § 112(6) (post AIA 112(f)) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112(6) (post AIA 112(f)) when such corresponding structures are not explicitly disclosed in the foregoing patent specification. Therefore, for any invention element(s)/structure(s) corresponding to functional claim limitation(s), in the below claims interpreted under 35 USC § 112(6) (post AIA 112(f)), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112(6) (post AIA 112(f)) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112(6) (post AIA 112(f)), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing the venting system according to the present invention will be apparent to those skilled in the art. Various aspects of the invention have been described above by way of illustration, and the specific embodiments disclosed are not intended to limit the invention to the particular forms disclosed. The particular implementation of the venting system may vary depending upon the particular context or application. By way of example, and not limitation, the venting system described in the foregoing were principally directed to HVAC implementations; however, similar techniques may instead be applied to portable air filtration systems, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

What is claimed is:

1. A system comprising:
    a base frame device configured to engage an exit register of an AC system, the base frame device including
        a metal base frame section,
        an open base frame space section, and
        a base frame securing hole configured to accept a securing means for securing the base frame device to the exit register;
    a register cover device configured to engage the base frame device, the register cover device including
        a plurality of alternating open space portions,
        a plurality of air diverting fin segments, and
        a magnet holder implement having at least four magnet holders, each magnet holder disposed at an end portion of a corner of the register cover device; and
    a magnet implement including at least four height adjustable magnets, each height adjustable magnet being disposed at a corresponding magnet holder among the at least four magnet holders and configured to magnetically engage the register cover device with the base frame device,
        wherein each height adjustable magnet is in frictional contact with the corresponding magnet holder such that the height adjustable magnet is movable within the magnet holder to adjust a height of each height adjustable magnet relative to the register cover device, each height adjustable magnet being tightly held by the magnet holder once a selected height is achieved.

2. The system of claim 1, wherein the register cover device further comprises at least four register cover pre-cut holes, each pre-cut hole disposed at a corresponding corner of the register cover device and configured to hold a corresponding magnet holder among the at least four magnet holders.

3. The system of claim 1 further comprising a plurality of open space segments configured to accommodate a louver handle.

4. The system of claim 1, wherein the register cover device further comprises a sidewall having a predetermined height, wherein the predetermined height of the sidewall section is configured to:
    allow each of the four height adjustable magnets a free range of up and down motion in the corresponding magnet holder until the selected height is achieved such that each of the four height adjustable magnets is in direct contact with the base frame device,
    accommodate a filter appliance, or
    allow each of the four height adjustable magnets a free range of up and down motion in the corresponding magnet holder until the selected height is achieved such that each of the four height adjustable magnets is in direct contact with the base frame device, and accommodate a filter appliance.

5. The system of claim 1, wherein the register cover further comprises an indented segment configured as a filter appliance holding area and operable for making an installation or removal of the filter appliance easier.

6. The system of claim 5 further comprising a filter appliance disposed in the indented segment, wherein the filter appliance is configured to filter air contaminants and impurities blowing through the exit register.

7. The system of claim 6, wherein the filter appliance further comprises at least four filter pre-cut holes positioned to correspond to positions of the at least four height adjustable magnets.

8. The system of claim 6, wherein the filter appliance comprises at least an activated carbon filter that is configured to chemically absorb contaminants, impurities and light odors from air blowing through the exit register.

9. The system of claim 6, wherein the filter appliance includes an antibacterial filter media that is configured to inhibit growth of microorganisms.

10. The system of claim 6, wherein the filter appliance includes at least one of an allergy-free filter media and an odor reduction filter media that is configured to capture dust, lint, smoke, mold, mildew, or pollen.

11. The system of claim 1, wherein about half of the plurality of air diverting fin segments are pointed to a proximate left side and about half of the plurality of air diverting fin segments are pointed to a proximate right side of the register cover device.

12. The system of claim 1 further comprising:
    at least four pre-cut holes, each pre-cut hole disposed at a corresponding corner of the register cover device and configured to hold a corresponding magnet holder among the at least four magnet holders;

a plurality of open space segments configured to accommodate an existing louver handle; and a sidewall section having a predetermined height, configured to at least one of allow each height adjustable magnet a free range of up and down motion to adjust the height of the height adjustable magnet such that the height adjustable magnet is in direct contact with the base frame device, and to accommodate a filter appliance.

13. A system comprising:
a register cover including:
   a plurality of alternating openings and air diverting fin segments, and
   a magnet holder; and
a height adjustable magnet disposed in the magnet holder, wherein the height adjustable magnet is in frictional contact with the magnet holder and is movable within the magnet holder to adjust a height of the height adjustable magnet relative to the register cover, and the height adjustable magnet is tightly held by the magnet holder once a selected height is achieved.

14. The system of claim 13, wherein the register cover further defines a pre-cut hole configured to hold the magnet holder.

15. The system of claim 13, wherein the register cover includes an opening configured to accommodate a louver handle.

16. The system of claim 13, wherein the register cover includes an indented segment.

17. The system of claim 16 further comprising a filter appliance disposed in the indented segment of the register cover.

18. The system of claim 17, wherein the filter appliance includes a pre-cut hole positioned to correspond to a position of the height adjustable magnet.

19. A system comprising:
a frame;
a register cover including:
   a plurality of alternating openings and air diverting fin segments, and
   a plurality of magnet holders; and
a plurality of height adjustable magnets disposed in a corresponding magnet holder among the plurality of magnet holders, wherein each height adjustable magnet is in frictional contact with its corresponding magnet holder and movable within the magnet holder to adjust a height of the height adjustable magnet relative to the register cover, and the height adjustable magnet is tightly held by the magnet holder once a selected height is achieved such that the height adjustable magnet is in direct contact with the frame.

20. The system of claim 19 further comprising a filter appliance disposed in the register cover, the filter appliance having a plurality of pre-cut holes, each precut hole corresponding to a position of one of the height adjustable magnets.

* * * * *